United States Patent
Brennan et al.

[19]

[11] Patent Number: 6,161,437
[45] Date of Patent: Dec. 19, 2000

[54] METHOD AND APPARATUS FOR EVALUATING AN ANALYTE

[75] Inventors: Kevin F. Brennan, Atlanta; William Daniel Hunt, Decatur, both of Ga.

[73] Assignee: Georgia Tech Research Corporation, Atlanta, Ga.

[21] Appl. No.: 09/289,405

[22] Filed: Apr. 9, 1999

Related U.S. Application Data

[60] Provisional application No. 60/081,168, Apr. 9, 1998.

[51] Int. Cl.$^7$ ....................................................... G01D 5/32
[52] U.S. Cl. ............................... 73/655; 422/50; 435/808; 436/805; 436/807
[58] Field of Search ............................... 73/570, 649, 655, 73/657, DIG. 4; 422/50; 438/50; 356/311, 300, 317, 318; 436/516, 805, 807, 527, 518, 524, 525, 164; 435/808, 4, 7.1

[56] References Cited

U.S. PATENT DOCUMENTS

| | | | |
|---|---|---|---|
| 4,932,255 | 6/1990 | Brace et al. | 73/204.11 |
| 5,035,863 | 7/1991 | Finlan et al. | 422/82.05 |
| 5,322,798 | 6/1994 | Sadowski | 436/113 |
| 5,325,704 | 7/1994 | Mariani et al. | 73/24.06 |
| 5,327,225 | 7/1994 | Bender et al. | 356/445 |
| 5,351,127 | 9/1994 | King et al. | 356/445 |
| 5,374,563 | 12/1994 | Maule | 436/165 |
| 5,415,842 | 5/1995 | Maule | 422/82.05 |

(List continued on next page.)

OTHER PUBLICATIONS

Print–Out of Web Page Entitled "Biosening with SPR", located at URL http://www.chem.vt.edu/chem–dept/students/Earp/intro3.html, Initial Publication Date Unknown but Printed on Mar. 30, 1999.

Print–Out of Web Page Entitled "Surface Plasmon Resonance SPR", located at URL http://barolo.ipc.uni–tuebingen.de/informat/spr/index.html, Initial Publication Date Unknown but Printed on Mar. 30, 1999.

Print–Out of Web Page Entitled "S+M Siemens Matsushita Components, Two Filters for the Size of One", Initial Publication Date Unknown but Printed on Mar. 30, 1999.

Print–Out of Web Page Entitled "S+M Siemens Matsushita Components, New SAW Filters for Consumer Electronics", Initial Publication Date Unknown but Printed on Mar. 30, 1999.

(List continued on next page.)

*Primary Examiner*—Richard A. Moller
*Attorney, Agent, or Firm*—Thomas, Kayden, Horstemeyer & Risley, L.L.P.

[57] ABSTRACT

The present invention is directed to a combined SAW sensor and a SPR sensor for evaluating an analyte, as well as a novel method for evaluating an analyte by utilizing a surface acoustic wave (SAW) sensor to determine the mass of the analyte and utilizing a surface plasmon resonance (SPR) sensor to determine the permittivity of the analyte. In accordance with one aspect of the invention, an apparatus is provided for evaluating an analyte. In one embodiment, the apparatus includes a piezoelectric substrate, a SAW sensor disposed on the substrate, and a SPR sensor disposed on the substrate in close proximity to the SAW sensor. In another embodiment, the apparatus more broadly includes a SAW sensor and a SPR sensor coupled to the surface acoustic wave sensor. In a preferred embodiment, the apparatus the SAW sensor includes two interdigital transducers and a chemically sensitive film interposed between the two interdigital transducers. The apparatus further includes an acousto-optic tunable filter (AOTF) disposed on the substrate, and interposed between the SAW sensor and the SPR sensor. The AOTF functions to couple the SAW sensor and the SPR sensor. The SPR sensor includes a chemically sensitive film, and an acoustic absorber is disposed on the substrate and interposed between the AOTF and the chemically sensitive film of the SPR sensor. Finally, an optical fiber may be configured to introduce a broadband light into the substrate, the optical fiber disposed to direct the light through the AOTF, the acoustic absorber, and the chemically sensitive film of the SPR sensor.

25 Claims, 4 Drawing Sheets

U.S. PATENT DOCUMENTS

| | | | |
|---|---|---|---|
| 5,485,277 | 1/1996 | Foster | 356/445 |
| 5,492,840 | 2/1996 | Malmqvist et al. | 436/518 |
| 5,561,069 | 10/1996 | Brigham-Burke et al. | 436/518 |
| 5,821,425 | 10/1998 | Mariani et al. | 73/703 |
| 5,846,610 | 12/1998 | Sunderland | 427/534 |
| 5,846,843 | 12/1998 | Simon | 436/527 |
| 5,858,799 | 1/1999 | Yee et al. | 436/164 |
| 5,965,456 | 10/1999 | Malmqvist et al. | 436/514 |

OTHER PUBLICATIONS

Print–Out of Web Page Entitled "S+M Siemens Matsushita Components, Success Through Innovation", Initial Publication Date Unknown but Printed on Mar. 30, 1999.

Print–Out of Web Page Entitled "Phonon Corporation—SAW Market Summary", located at URL http://www-.phonon.com/old/market.html, Initial Publication Date Unknown but Printed on Mar. 30, 1999.

Print–Out of Web Page Entitled "Vectron Products—Surface Acoustic Wave (SAW—Index)", located at URL http://www.vectron.com/products/saw/saw_index.htm, Initial Publication Date Unknown but Printed on Mar. 30, 1999.

Print–Out of Web Page Entitled "Surface–Acoustic Waves", located at URL http://www.focus.hut.fi/annrep/1996/node32.html, Initial Publication Date Unknown but Printed on Mar. 30, 1999.

Print–Out of Web Page Entitled "SAW—Surface Acoustic Wave Sensor for Testing the Quality of the Paper Surface", located at URL http://lisa.polymtl.ca/Projects/SAW.html, Initial Publication Date Unknown but Printed on Mar. 30, 1999.

Print–Out of Web Page Entitled "What Will You Do With Spreeta Technology", located at URL http://www.ti.com/sc/docs/msp/spreeta/what.htm, Initial Publication Date Unknown but Printed on Mar. 30, 1999.

Print–Out of Web Page Entitled "Phonon Corporation—What is a SAW Device?", located at URL http://www-.phonon.com/old/what.html, Initial Publication Date Unknown but Printed on Mar. 30, 1999.

Print–Out of Web Page Entitled "Fiber SPR Sensors", located at URL http://www.phonon.chem.vt.edu/chem–dept/students/Earp/intro2.html.

Print–Out of Web Page Entitled "Operation Landmine: New Technology", located at URL http://www.opusa.org/opland/caen.html, Initial Publication Date Unknown but Printed on Mar. 30, 1999.

Print–Out of Web Page Entitled "Defense—Spreeta Technology at TI", located at URL http://www.ti.com/sc/docs/msp/spreets/defense.htm, Initial Publication Date Unknown but Printed on Mar. 30, 1999.

Print–Out of Web Page Entitled "Surface Plasmon Resonance Introduction", located at URL http://www.chem.vt-.edu/chem–dept/students/Earp/intro1.html, Initial Publication Data Unknown but Printed on Mar. 30, 1999.

METHOD AND APPARATUS FOR EVALUATING AN ANALYTE

CROSS-REFERENCE TO RELATED APPLICATION

This application claims the benefit of U.S. Provisional Patent Application, Ser. No. 60/081,168, filed Apr. 9, 1998, and entitled "Integrated Surface Acoustic Wave-Surface Plasmon Resonance Sensors," which is hereby incorporated by reference in its entirety.

This invention was developed pursuant to U.S. Navy/Naval Coastal Systems Contract No.: N6 1331-85-D-0025-0006. Accordingly, the U.S. Government has a paid-up license in this invention.

BACKGROUND OF THE INVENTION

1. Field of the Invention

The present invention generally relates to electronic sensors, and more particularly to the fields of surface acoustic wave sensors and surface plasmon resonance sensors.

2. Discussion of the Related Art

There are a variety of situations in which it is desirable to idetifty a target analyte by evaluating an air sample near the object or other material. For example, canines have long been used to locate hidden drugs and identify land mines. Indeed, hidden land mines continue to pose a significant threat to civilians worldwide. As a result of wars and other armed conflicts, many millions of unexploded land mines remain buried over some 60 countries worldwide. It has even been reported by the International Committee of the Red Cross that land mines claim a victim every 20 minutes. Presently, the discovery and removal of these explosives is a very tedious and expensive process. Accordingly, rapid, and cost-effective detection is key to the timely removal of the millions of land mines already scattered worldwide. Alternatives to metal detectors include some technologies that are also being developed for detection of bombs and unexploded ordnance. Some biologically based approaches have been suggested.

More specifically, surface acoustic wave (SAW) technology has been proposed as one possible manner of more rapidly detecting land mines. As is known, when an electric field is applied to a piezoelectric material, a sound wave of specific frequency can be generated on the surface. The frequency of the surface acoustic wave varies based upon the material and its surface characteristics. Accordingly, certain objects and materials can, essentially, produce a SAW frequency signature. In this way, identification of the frequency signature identifies the target analyte. Nominally, the SAW sensor measures the mass of the target analyte.

Surface plasmon resonance (SPR) technology is another technological field that is used to identify target analytes. SPR has been known for over 20 years and is used to identify the dielectric permittivity of the target analyte. As is known, SPR is the oscillation of the plasma of free electrons which exists at a metal boundary. These oscillations are affected by the refractive index of the material adjacent the metal surface. SPR may be achieved by using the evanescent wave which is generated when a TM-polarized light beam is totally internally reflected at the boundary of a medium, e.g., glass, which has a high dielectric constant.

In general, an SPR configuration includes a source of electromagnetic radiation (light), an optically transmissive (transparent) component (the SPR sensor) which has a conducting film (e.g. a metal layer) on it, and a detector. The conducting film is in contact with a dielectric. Light is transmitted into the transparent component, undergoes total internal reflection, and if the conditions outlined in the equations above are met, then a surface plasmon wave will occur at the surface of the conducting film, that is at the interface of the metal layer and the dielectric. The detector measures the resonant phenomenon.

To illustrate, reference is made to FIG. 1, which is a diagram that illustrates a setup for evaluating SPR. A beam 1 of light is directed from a laser source (not shown) onto an internal surface 2 of a glass body 3. A detector (not shown) monitors the internally reflected beam 4. Applied to the external surface 2 of glass body 3 is a thin film 5 of metal, for example gold or silver, and applied to the film 5 is a further thin film 6 of organic material containing antibodies. A sample 7 containing antigen is brought into contact with the antibody film 6 to thus cause a reaction between the antigen and the antibody. If binding occurs, the refractive index of the film 6 will change owing to the increased size of the antibody molecules, and this change can be detected and measured using surface plasmon resonance techniques.

Sensors based on the SPR effect sense the refractive index (RI) of a thin region adjacent to the sensing surface. SPR can be applied indirectly to other sensing applications by treating or manipulating the sensing surface such that the refractive index at the surface varies with the presence of the substance to be sensed. For instance, the surface can be made sensitive to a particular antibody by coating the surface with an antigen for that antibody. When the antigen binds to the antibody, the refractive index at the surface changes slightly. A commercial application of SPR to biological sensing has been developed using this principle.

The practical effect of a change in the RI of the dielectric adjacent to the SPR sensing surface is a shift in the SPR resonance curve. If the wavelength modulation technique is being used, the resonance curve of interest is the reflected intensity of light versus the incident wavelength. The minimum of this curve is defined as $\lambda_{sp}$, which is the SPR resonance minimum in wavelength space. If the angle modulation technique is being used, the resonance curve of interest is the reflected intensity of light versus the incident angle. The minimum of this curve is defined as $\theta_{sp}$, which is the SPR resonance minimum in angle space. It is also possible to determine the resonance from looking at the transmitted light intensity using either of these techniques. The techniques can also be combined, in which case the three dimensional intensity-angle-wavelength space must be considered. The absorption of the dielectric layers, which is directly related to the imaginary part of the refractive index of the dielectric layers, can also be determined from the SPR resonance. More absorbing dielectric layers, such as dye indicators (for instance, methylene blue), cause broader, less deep resonances. Parameters such as the resonance depth, or the resonance width, are not used as much as the resonance minimum location, because SPR is much more sensitive to changes in the real part of the index of refraction than it is to changes in absorption.

Though SPR detection and evaluation techniques have been demonstrated and has been shown to yield a high degree of sensitivity, the required set up has proven useful only in a laboratory or highly controlled setting. The primary limitations to usage of standard SPR setups are (1) they are large and unwieldy, and cannot readily be made compact, (2) they must be carefully isolated from shock and external vibration, and (3) the cost of the entire system is relatively high. All of these effects make the standard SPR setups of little use in field portable systems or remote sensing applications.

Accordingly, there is a heretofore unaddressed need to provide a remote or field sensor configuration for detecting and/or measuring an analyte in a field setting.

SUMMARY OF THE INVENTION

Certain objects, advantages and novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the advantages and novel features, the present invention is generally directed to a novel apparatus and method for evaluating an analyte (target object or material). Broadly, the present invention is the combination of a SAW sensor and a SPR sensor. Likewise, and in accordance with another aspect of the present invention, a method is provided for evaluating an analyte by utilizing a surface acoustic wave (SAW) sensor to determine the mass of the analyte and utilizing a surface plasmon resonance (SPR) sensor to determine the permittivity of the analyte.

In accordance with one aspect of the invention, an apparatus is provided for evaluating an analyte. In one embodiment, the apparatus includes a piezoelectric substrate, a SAW sensor disposed on the substrate, and a SPR sensor disposed on the same substrate in close proximity to the SAW sensor. In another embodiment, the apparatus more broadly includes a SAW sensor and a SPR sensor coupled to the surface acoustic wave sensor.

In a preferred embodiment, the apparatus the SAW sensor includes two interdigital transducers and a chemically sensitive film interposed between the two interdigital transducers. The apparatus further includes an acousto-optic tunable filter (AOTF) disposed on the substrate, and interposed between the SAW sensor and the SPR sensor. The AOTF functions to couple the SAW sensor and the SPR sensor. The SPR sensor includes a chemically sensitive film, and an acoustic absorber is disposed on the substrate and interposed between the AOTF and the chemically sensitive film of the SPR sensor. Finally, an optical fiber may-be configured to introduce a broadband light into the substrate, the optical fiber disposed to direct the light through the AOTF, the acoustic absorber, and the chemically sensitive film of the SPR sensor.

In the configuration of the embodiment described above, a frequency synthesizer may be used to drive the SAW sensor through an optical spectrum. Simultaneously, an output of the SPR sensor may be evaluated to detect a minimum transmissivity. The frequency of the frequency synthesizer at this minimum transmissivity corresponds may be readily measured. This frequency win differ when the chemically sensitive film is exposed to ambient, from the frequency when the chemically sensitive film is exposed to the analyte. The shift in the frequency can be readily measured and is used to determine the permissivity of the analyte.

The SAW sensor can be used separately, and in a manner that is known, to determine the mass of the analyte. In accordance with the invention, the two sensors are integrated and used in combination to provide improved accuracy in identifying an analyte, by reflecting both mass and permittivity of the analyte.

DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF THE PREFERRED EMBODIMENT

Figure 1:
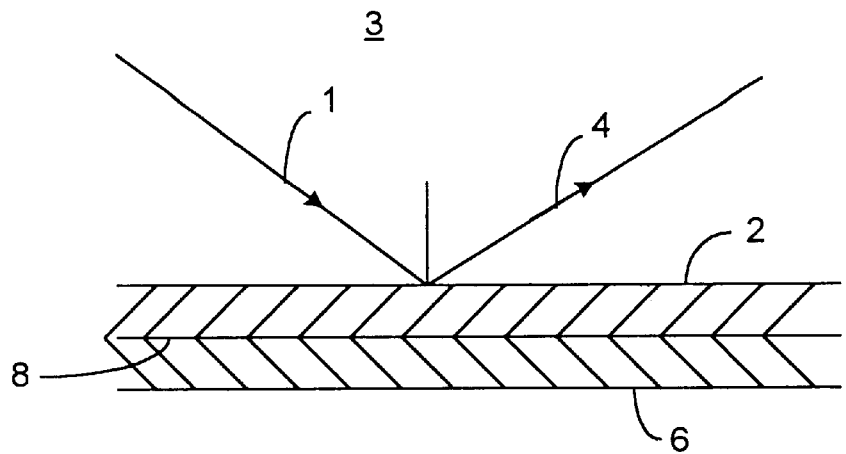
FIG. 1 is a diagram that illustrates the SPR effect, and its detection.

Having summarized various aspects of the present invention, reference will now be made in detail to the description of the invention as illustrated in the drawings. While the invention will be described in connection with these drawings, there is no intent to limit it to the embodiment or embodiments disclosed therein. On the contrary, the intent is to cover all alternatives, modifications and equivalents included within the spirit and scope of the invention as defined by the appended claims.

As summarized above, the present invention is directed to an apparatus and method for evaluating an analyte. The apparatus results from the novel combination of a SAW sensor and a SPR sensor. However, before describing the novel system and method of the present invention, SAW and SPR sensors and technology will be more fully described.

Surface Acoustic Waves

Figure 2:
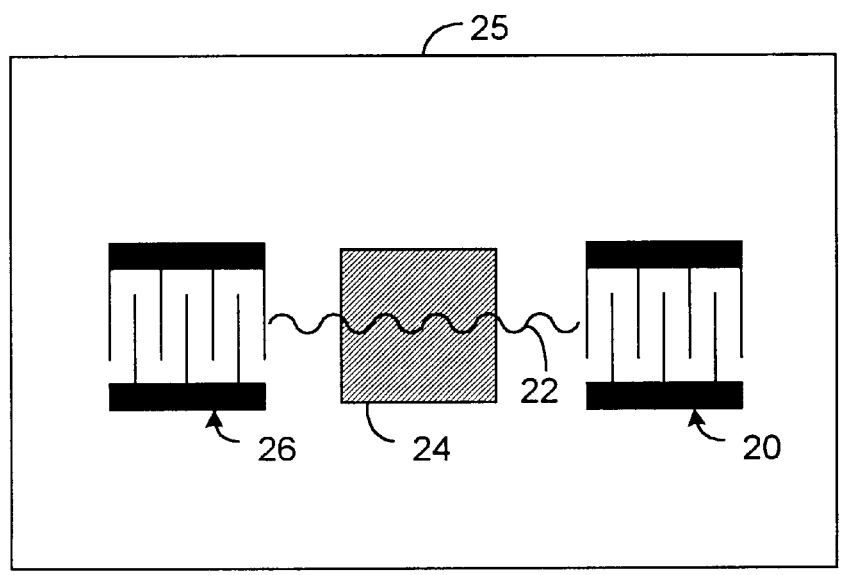
FIG. 2 is a diagram illustrating a conventional SAW sensor, as is known in the art.

Turning now to the drawings, reference is made to FIG. 2, which illustrates a SAW sensor, as is known in the prior art. As is known, SAW devices basically consist of an input transducer 20 to convert electrical signals to tiny acoustic waves 22, which then travel through a solid propagation medium 24 to an output transducer 26 where they are reconverted to electrical signals. More specifically, and as shown the input transducer may include an interdigital transducer 22, and the output transducer 26 may comprise a similar interdigital transducer. The input transducer converts an oscillating electric signal into acoustic waves, which are propagated through a substrate 25 that interconnects the input transducer 22 and the output transducer 26. A chemically sensitive film 24 may also be interposed between the input transducer 22 and the output transducer 26. The output transducer 26 generates an oscillator electrical signal, in response to the acoustic signal propagated from the input transducer 22.

In a manner that is known, the SAW sensor may be configured in an oscillator loop, where the output electrical signal may be input to an amplifier (not shown) and fed back to the input transducer. This oscillator loop will resonate at the resonant frequency of the chemically sensitive film. When the chemically sensitive film is exposed to ambient, this resonant frequency will be a first value. The resonant frequency, however, will change to a different value, however, when the chemically sensitive film is exposed to an analyte. The change in the resonant frequency can be used to ascertain the mass of the analyte.

Surface Plasmon Resonance

As mentioned above, a surface plasmon is an oscillation of free electrons that propagates along the surface of a conductor. Typically this conductor is a thin film of metal such as silver or gold, however surface plasmons have also been excited on semiconductors. The most common method of exciting surface plasmons is to couple the transverse-magnetic (TM) polarized energy contained in an evanescent field to the plasmon mode on a metal film. The amount of coupling, and thus the intensity of the plasmon, is directly affected by the refractive indices of materials on both sides of the metal film. By including the sample to be measured as a layer on one side of the film, changes in the refractive index of the sample can be monitored by measuring changes in the evanescent field to surface plasmon coupling efficiency. Surface plasmons represent the quanta of the oscillations of surface charges that are produced by application of an external electric field to a conducting medium.

Kretschmann Prism Arrangement

Figure 3:
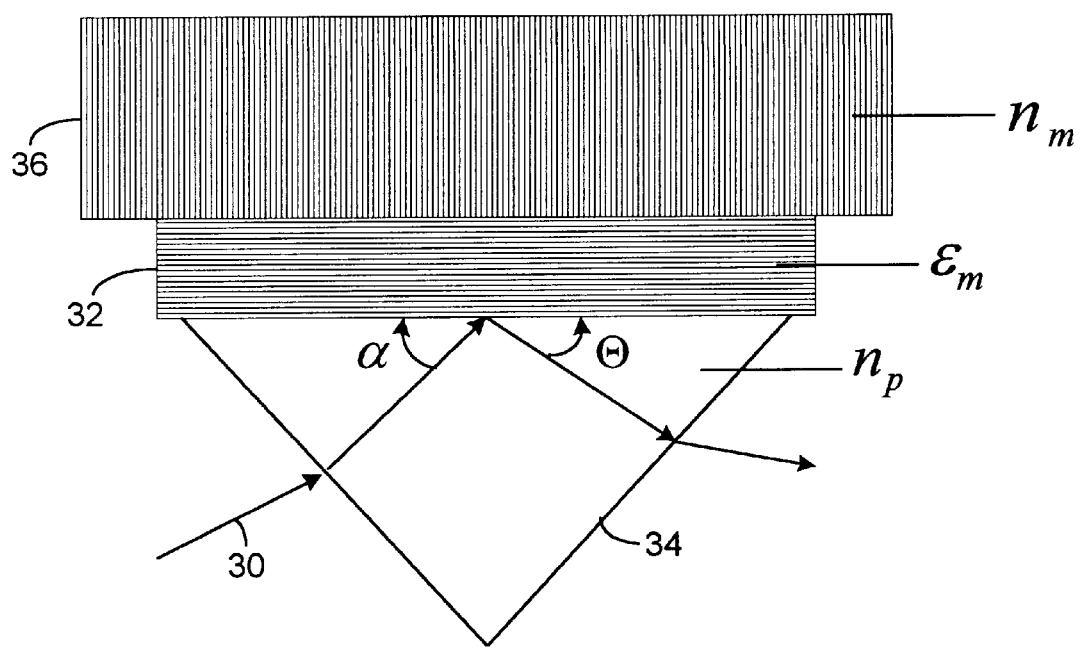
FIG. 3 is a diagram illustrating a Kretschmann prism arrangement for measuring SPR, as is known in the art.

With reference to FIG. 3, the Kretschmann prism arrangement is essentially a mechanism whereby a light ray 30 is coupled into the surface plasmon (SP) mode that can exist on a metal film. The SP can be described as an oscillation of electrons on the surface of a solid, typically a conductor but SP waves have been generated on the surface of semiconductors as well. Commonly used to support the SP are thin conductive films. Gold or silver films are most often used due to their relative ease with which they can be deposited onto a substrate with an accurate thickness. The surface chemistry of gold and its resistance to oxidation make it the prime choice for SPR experiments although many other materials can support SP waves. The main criteria for a material to support SP waves is that it have a negative real dielectric component. Although materials other than metals can support SPR, metals are most commonly used and will be used to denote a support surface for SP waves.

The thin film that will be used for support of the SP will be surrounded on both sides by a dielectric material. The SP can exist at the metal-dielectric interface within which it is possible to have components of an external electric field, E, present in both media. This electric field will have a distribution throughout the interface which will begin or end at charges contained on each of the interface constituents. Trapped within the interface is the SP mode which has an electric field that decays into the surroundings. This surface mode will be bound to a charge density wave of electrons oscillating on the metal film and will be greatly influenced by changes in optical properties of the surroundings.

In this classical technique, known as the Kretschmann prism arrangement, a thin film of metal 32 is coated on one face of a prism 34 which has a high refractive index. This metal surface forms the transduction mechanism for the sensor and is brought into contact with the sample 36 to be sensed. Light is launched into the prism 34 and reflected off the metal film 32 to an optical photodetector (not shown) to create the sensor output.

The light launched into the prism 34 and coupled into the SP mode on the film is TM-polarized with respect to the metal surface where the reflection takes place. Only TM-polarized light can be coupled into the plasmon mode because this particular polarization has the electric field vector oscillating normal to the plane that contains the metal film. This is sometimes referred to as the transverse magnetic or (TM) polarization. The surface plasmon is affected by changes in the dielectric value so materials in contact with the metal film. As these values change, the conditions necessary to couple light into the plasmon mode also change. For the particular sensing system described in FIG. 3, the angle of incidence for the light beam with respect to the metal surface and the reflected light intensity will be the measured parameters of interest. If the angle α of incidence for the light beam is scanned throughout a range of values, a distinct minimum in reflectivity will be observed at a discrete angle θ associated with a given refractive index sample. This angle will be known as θsp, the surface plasmon coupling angle. At this particular angle in incidence, set of dielectric values, and optical wavelength, light is being coupled into the plasmon mode and the reflection is attenuated.

As previously discussed, under normal conditions light launched into the prism 34 cannot couple into a plasmon mode. Light couples into the SP mode via the evanescent wave that is generated at the prism-metal boundary when the light beam is totally internally reflected. This coupling of light into the plasmon mode causes the attenuation of light at the detector. Sensing is carried out by relating θsp to changes in the dielectric values or refractive index of the sample. Assuming TM-polarized laser light to couple into the plasmon mode fixes the wavelength a particular value. Fixing the wavelength also to specify the values of nm and np at that wavelength. There are two parameters left, θ and ns. Choosing a sample to investigate will fix ns and therefore will only have θ to contend with. Small changes in the refractive index of the sample can therefore be monitored by measuring the plasmon coupling angle, θsp, or the time derivative of θ. SPR is a highly sensitive technique useful for investigating changes that occur at the surface of the metal film.

Combined SAW and SPR Sensors

Having set forth certain fundamental information about SAW and SPR sensors, as is known in the prior art, reference will be made in more detail about the present invention. As previously mentioned, the present invention is directed to a novel a field sensor for detecting an analyte that integrates a novel combination of SPR and SAW sensors. In this regard, reference is made to FIG. 4, which illustrates a first embodiment of the present invention. Illustrated in the figure is a portion of a field sensing device that includes a SAW sensor 102 and a SPR sensor 104, integrated on a single substrate 100, such as a piezoelectric substrate. In a manner that will be described below the SAW sensor 102 is coupled to the SPR sensor 104 through an acousto-optic tunable filter (AOTF) 106. It should be appreciated that the term "piezoelectric substrate" should be construed broadly. For example, the term piezoelectric substrate, as used herein, includes substrates coated with a piezoelectric film. For example, a silicon substrate having a piezoelectric film sputtered thereon.

As described above in connection with the description of a conventional SAW sensor, the SAW sensor 102 includes a pair of interdigital transducers 108 and 110, disposed on both sides of a chemically film 112, which is usually applied on a gold film. The transducers 108 and 110 are referred to as interdigital transducers, because the include a plurality of alternating digits extending between a pair of buss bars. Transducer 108 is an input transducer that receives an alternating electrical signal, applied across the buss bars, and the alternating digits generate an acoustic signal, in the form of acoustic waves. These waves propagate through the film 112, which is also disposed on the substrate 100, and is interposed between the input transducer 108 and the output transducer 110.

The acoustic waves generated by the input transducer 108 are received by the digits of the output transducer 110, which generates an alternating electrical signal across its buss bars. This, relatively low amplitude electrical signal is passed through an amplifier 114, and is directed back to the input transducer 108. This feed back configuration is referred to as an oscillator loop. In the illustrated embodiment, the electrical signal may be routed from the amplifier 114 to the input transducer 108, through a RF switch 116. The purpose of the RF switch will be better appreciated from the discussion below. In short, the oscillator loop configuration of the SAW sensor 102 will resonate at the resonant frequency of the loop system, which will be largely determined by the properties of the film 112.

When the film 112 is exposed to ambient conditions, the SAW sensor 102 will oscillate at a first resonant frequency. When, however, the film 112 is exposed to alternative environmental conditions, the SAW sensor 102 will oscillate at a second resonant frequency. The difference between the first resonant frequency and the second resonant frequency reflects a change in mass of the chemically sensitive film 112. In a manner that is known, the chemically sensitive film 112 may be selected to react with a target analyte. For example, if the sensor is to be used for detecting land mines, then the chemically sensitive film may be selected to react appropriately. Likewise, if the sensor is to be used for detecting cocaine, then a different chemically sensitive film may be selected. A chemically specific film is one technique for improving the sensor's ability to identify a specific target analyte in the presence of interfering analytes. The sensor assembly illustrated herein depicts only a single SAW sensor 102 and a single SPR sensor 104. In will appreciated that this may be all that is necessary if films 112 and 122 having a high chemical specificity (e.g., an antibody film) are chosen. If, however, the films 112 and 122 use a relatively low chemical specificity, then the assembly will preferable comprise an array of SAW and SPR sensors. The size of the sensor assembly will, of course, depend upon the number of sensors utilized.

It will be appreciated that the sensor may be configured in such a way that an air flow is established across the chemically sensitive film 112. In this regard, a fan may be used to establish such an air flow. The sensor assembly may be disposed on a wand or other extension, so that it may readily be moved to interrogate areas a small distance from the user. If, for example, the sensor assembly is configured to detect land mines, when it is moved to the air space above a land mine, the fan (not shown) will direct the air in that area over the film 112, causing a change in the resonant frequency of the SAW sensor 102, as described above.

Turning now to the SPR sensor 104, this sensor is implemented in a drastically different approach than the prism or other three-dimensional optical reflection system of the prior art. Instead, the sensor is compressed into two dimensions by coupling the light into an optical waveguide within the substrate material. Like the SAW sensor 102, the SPR sensor 104 also includes a chemically sensitive film 122 that is disposed over a metal film (usually gold). Unlike the SAW sensor 102, however, the SPR sensor 104 is not configured in a feedback configuration to excite resonance. Instead, the SAW sensor is reconfigured in an AOTF configuration for the SPR sensor 104 to pre-filter an optical beam that is interrogating the SPR sensor area. In this regard, the SAW frequency may be in the range of 100 MHz, and the AOTF 106 may be configured to have a wavelength bandwidth of approximately 50 Å.

As illustrated, a waveguide, such as an optical fiber 132, may be used to direct a broadband optical source to illuminate the SPR sensor 104. The optical source, which is preferably a laser light, is directed through a film region 106, across an acoustic absorber 120, and through the chemically sensitive film 122 of the SPR sensor 104. In the operational mode wherein the SPR sensor output is measured, the a portion of the SAW 102 is reconfigured. Specifically, a frequency synthesizer 130 is configured to generate an oscillating output in a manner whereby it sweeps through an optical range of frequencies. This output is directed to the interdigital transducer 108, by way of the RF switch 116. Thus, the RF switch 116 operates to pass the output of the amplifier 114 to the interdigital transducer 108, when the SAW sensor 102 is configured in an oscillator loop (for performing SAW sensing operation), and the RF switch 116 operates to pass the output of the frequency synthesizer 130 to the interdigital transducer 108, when configuring the assembly to perform SPR sensing.

When configured in this manner, the frequency synthesizer 130 causes the interdigital transducer 108 to propagate acoustic waves outward, in both directions, through the substrate 100. Due to the piezoelectric nature of the substrate 100, these acoustic waves also carry an electric component with them. These waves interact with the broadband transverse electric (TE) light, that is input to the device, within the region of the film 106 to convert the light to transverse magnetic (TM) light out. This TM light is then directed across an acoustic absorber 120, to deaden the acoustic waves. It should be appreciated that the acoustic absorber 120, prevents surface acoustic waves from propagating through chemically sensitive film 122 of the SPR sensor 104.

In operation, the AOTF 106 is configured to tune the optical signal such that, at any given time, the energy of only a 50 Å wavelength range interrogates the sensor 104. As the frequency synthesizer drives the interdigital transducer 108 through the optical spectrum, a detector 140 monitors the output of the SPR sensor 104 to identify a minimum in the transmissivity curve. Once this minimum is found, the frequency of the frequency synthesizer is noted.

Like the SAW sensor 102, which is monitored both in ambient conditions and in target conditions, the SPR sensor 104 is likewise monitored in differing conditions. When monitored in ambient conditions, the transmissivity minimum will occur at a first frequency of the frequency synthesizer 130. When monitored in target conditions, the transmissivity minimum will occur at a second frequency of the frequency synthesizer 130. The frequency differential between the first frequency and the second frequency corresponds to the permissivity of the material that has reacted with the chemically sensitive film 122. For a target analyte, a predetermined frequency differential will be designated. Thus, when the frequency differential equals this specified, predetermined value, the SPR sensor 104 will identify the target analyte.

In the illustrated embodiment, a second metal film 124 (preferably gold) is also disposed near the metal film 122 that is coated with a chemically sensitive material. As illustrated, the same TM light may be coupled through both films 122 and 124. Therefore, the target analyte will be incident upon both. Again, the chemical material (e.g. polymer, antibody film) disposed on the film 122 will be selected to have an affinity to react with a predetermined target analyte. The uncoated film 124 would have indiscriminate affinity, and is hence kept out of the analyte stream. By observing the reaction of both films, the detector 140 may be configured to obtain a better signal to noise ratio, and thus more accurate results.

In operation, the SAW sensor 102 and the SPR sensor 104 preferably will be configured to operate in alternative, but near instantaneous fashion. That is, the SAW sensor will be configured in an oscillator loop, as described above, and the resonant frequency may be observed by a frequency detector 142. As illustrated, the frequency detector 142 may be coupled (e.g., via RF) to the signal output from the amplifier 114. The resonant frequency will be known for a reference oscillator, so that a comparison may be readily made to this known value. Then, the RF switch 116 may configure the interdigital transducer 108 to operate in conjunction with the AOTF 106, to configure the SPR sensor 104 for operation, and vice-versa. It should be appreciated that the switching and measurements between the SAW sensor 102 and the SPR sensor 104 may be made on the order of microseconds, and therefore for all practical purposes it is as though a continuous monitoring of both sensors is performed.

It will be appreciated that the combined SAW/SPR sensor of the present invention provides a small, field-operable assembly that can effectively interrogate a target analyte for both mass and permittivity. Both of these qualities can be used to identify a target analyte. In some embodiments, such as mine detection, where the identification of false positive identifications are permissible, the outputs of the two sensor detectors 140 and 142 may be ORed, whereby the assembly may indicate a positive reading, if either of the sensors registers a positive reading. In other embodiments, such as drug detection, the assembly may be configured to AND the output of the two sensor detectors 140 and 142, whereby the assembly indicates a positive reading only if both sensors register a positive reading.

Figure 4:
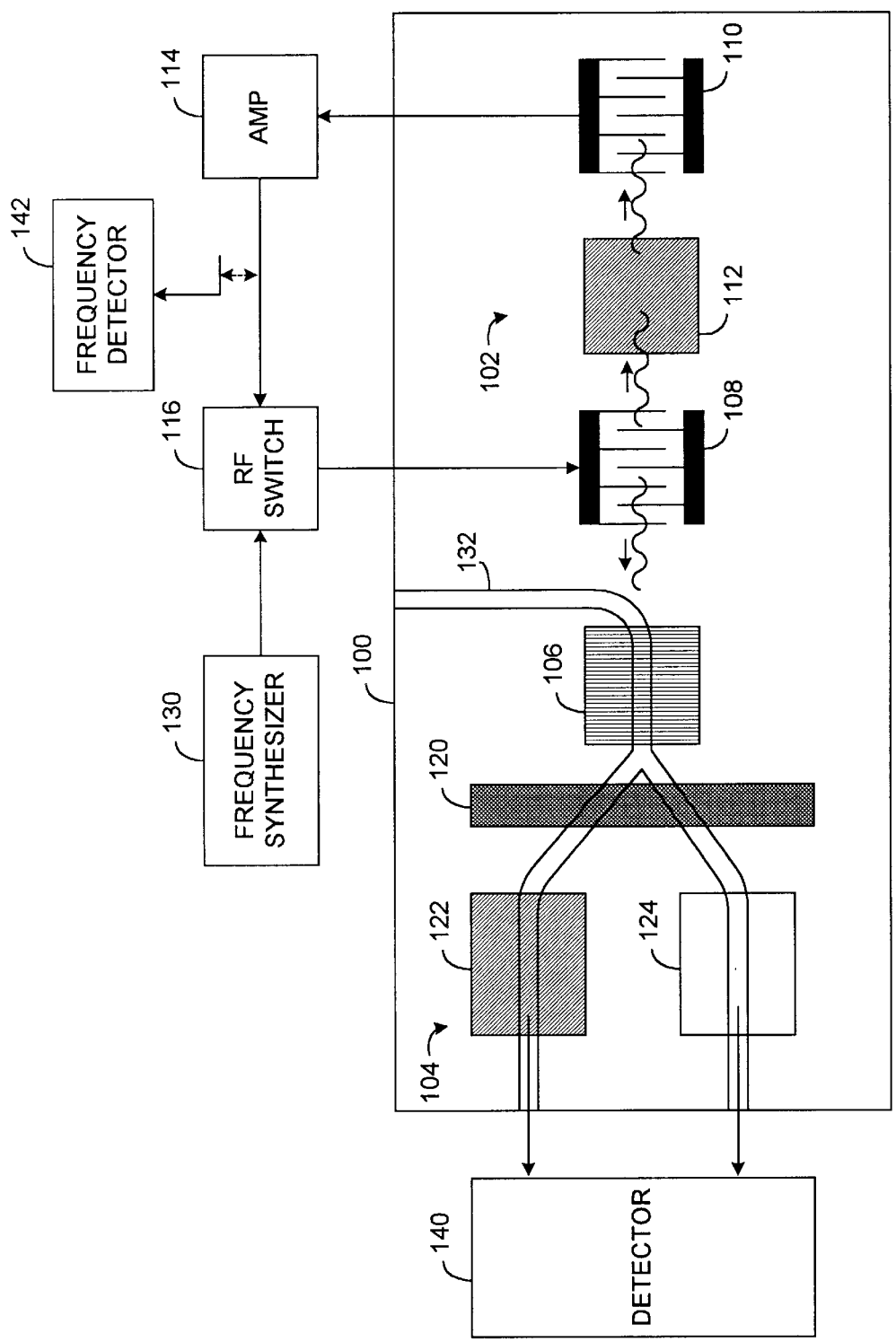
FIG. 4 is a diagram illustrating a combined SPR and SAW sensor, in accordance with one embodiment of the present invention.

Although the sensors 102 and 104 of the assembly of FIG. 4 will be disposed in relatively close proximity, one potential shortcoming of such an embodiment relates to the fact that two separate chemical sensitive sensors 112 and 122 are utilized. As a result, the two sensors 102 and 104 are not evaluating the identical air sample. Accordingly, an alternative configuration may be provided, like that shown in FIG. 5.

Although not specifically illustrated in FIG. 4, is will be appreciated by persons skilled in the art that an additional SAW sensor may be included to provide a reference frequency for comparison. More particularly, a second SAW sensor (not shown) may be disposed in close proximity to the SAW sensor 102, but isolated from the analyte stream. This additional sensor may be used to generate a reference frequency, that will be subject to the same temperature conditions as the SAW sensor 102. Therefore, frequency shifts that are due to temperature change, may be readily identified and factored into the calculations for identifying the target analyte mass.

Figure 5:
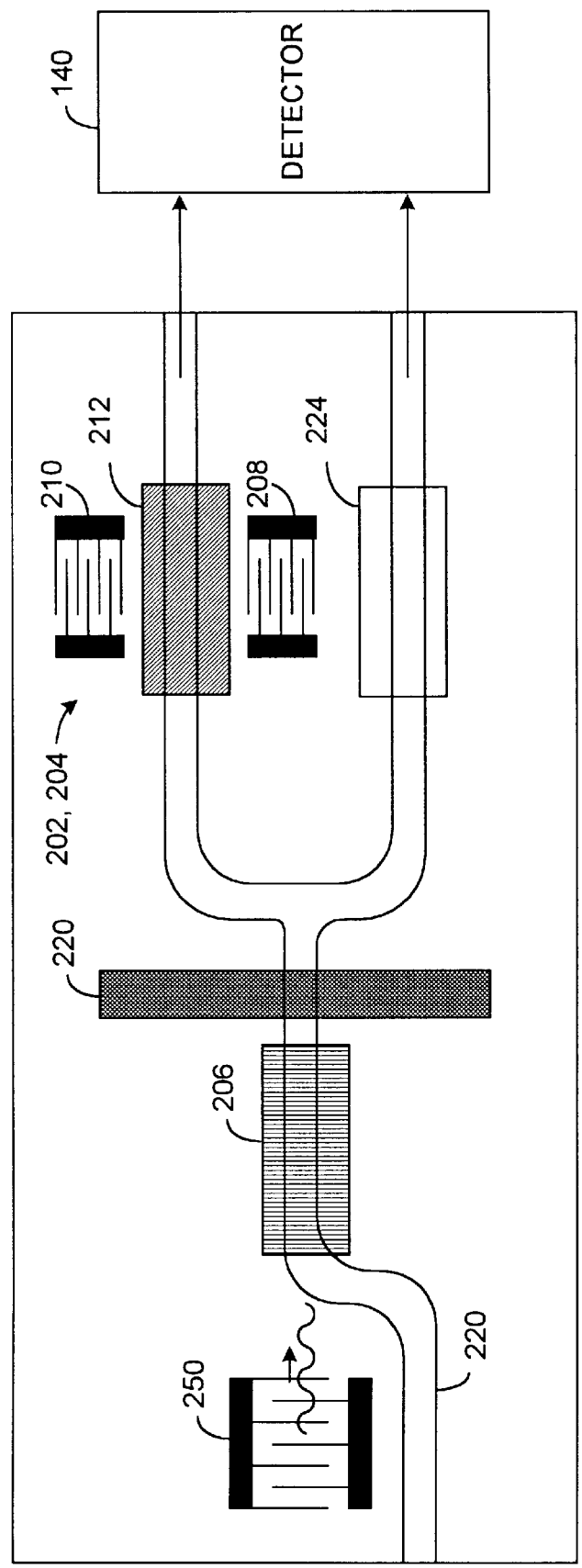
FIG. 5 is a diagram illustrating a combined SPR and SAW sensor, in accordance with another embodiment of the present invention.

The configuration of FIG. 5 is very similar to the configuration of FIG. 4, except that only one chemically sensitive film 212 is used, in place of the two films 112 and 122 illustrated in the configuration of FIG. 4. The SAW sensor 202 includes two interdigital transducers 208 and 210, that are configured on opposite sides of the film 212, and the SAW sensor 202 operates in the same fashion as the SAW sensor 102. The sensor assembly also includes a optical fiber 232 to direct an incoming broadband optical signal (TE light in) through an AOTF 206, an acoustic absorber 220, and through the chemically sensitive film 212. An additional interdigital transducer 250 is provided to propagate the acoustic waves that are responsible for controlling the AOTF 206. It will be appreciated that a frequency synthesizer (not shown in FIG. 5) will be configured to drive the interdigital transducer 250, in the same manner as that described in connection with FIG. 4. Also, a separate segment of metal (preferably gold) film 224 is also provided, so that the detector 240 may compare the output from both films 212 and 224.

Like the configuration described in FIG. 4, the SAW sensor 202 and the SPR sensor 204 will be operated in succession, but not simultaneously. Nevertheless, due to the high speed of operations, a user may operate the assembly to effectively receive real time, continuous monitoring of both sensors.

Accordingly, what has been provided is a novel sensor assembly that combines a SAW sensor and a SPR sensor, to evaluate both mass and permissivity of a target analyte.

It will be appreciated that other embodiments of the invention may be implemented, consistent with the broader concepts and teachings set forth herein. For example, an array of SPR sensors and an array of SAW sensors could be disposed in a single sensor assemble, wherein the various sensors are characterized by chemically sensitive films, each having a different chemical layer for detecting different target analytes. Accordingly, a highly versatile sensing apparatus may be provided for sensing a variety of different target materials.

The foregoing description is not intended to be exhaustive or to limit the invention to the precise forms disclosed. Obvious modifications or variations are possible in light of the above teachings. In this regard, the embodiment or embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly and legally entitled.

What is claimed is:

1. An apparatus for evaluating an analyte comprising:

a substrate;

a surface acoustic wave (SAW) sensor disposed on the substrate; and a surface plasmon resonance (SPR) sensor disposed on the substrate in close proximity to the SAW sensor.

2. The system as defined in claim 1, wherein the substrate is a piezoelectric substrate.

3. The system as defined in claim 1, wherein the SAW sensor includes two interdigital transducers and a chemically sensitive film interposed between the two interdigital transducers.

4. The system as defined in claim 3, further including an acousto-optic tunable filter (AOTF) disposed on the substrate, and interposed between the SAW sensor and the SPR sensor.

5. The system as defined in claim 4, wherein the SPR sensor includes a chemically sensitive film.

6. The system as defined in claim 5, further including an acoustic absorber disposed on the substrate and interposed between the AOTF and the chemically sensitive film of the SPR sensor.

7. The system as defined in claim 6, further including means for introducing broadband light into the substrate.

8. The system as defined in claim 7, wherein the means includes an optical fiber extending through the AOTF, the acoustic absorber, and the chemically sensitive film of the SPR sensor.

9. An apparatus for evaluating an analyte comprising:

a surface acoustic wave (SAW) sensor; and a surface plasmon resonance (SPR) sensor coupled through a substrate to the surface acoustic wave sensor.

10. The system as defined in claim 9, further including an acousto-optic tunable filter (AOTF) disposed between the SAW sensor and the SPR sensor.

11. A method for evaluating an analyte to determine both mass and permittivity of the analyte comprsing the steps of:
  utiizing a surface acoustic wave (SAW) sensor to determine the mass of the analyte;
  utilizing a surface plasmon resonance (SPR) sensor to determine the permittivity of the analyte; and
  coupling the SAW and SPR sensors by at least one selected from the group consisting of: configuring the SAW and SPR sensors so that they share a commnon chemically sensitive film; and disposing the SAW and SPR sensors on a common substrate, to achieve a common analyte sampling.

12. The method as defined in claim 11, wherein a chemically sensitive film of the SPR sensor is the same chemically sensitive film of the SAW sensor.

13. The method as defined in claim 11, further including the step of introducing a broadband optical source to the SPR sensor.

14. The method as defined in claim 13, further including the step of coupling the SAW to the SPR through an acousto-optic tunable filter (AOTF).

15. The method as defined in claim 14, further including the step of driving a SAW transducer with a frequency synthesizer to scan through an optical spectrum.

16. The method as defined in claim 15, further including the step of evaluating an output of the SPR sensor to detect a minimum transmissivity, as the frequency synthesizer scans causes the SAW transducer to scan through the optical spectrum.

17. The method as defined in claim 16, further including the step of measuring the frequency of the SAW transducer at the point where the minimum transmissivity is detected.

18. A method for evaluating an analyte to determine both mass and permittivity of the analyte comprising the steps of:
  utilizing a surface acoustic wave (SAW) sensor to determine the mass of the analyte;
  utilizing a surface plasmon resonance (SPR) sensor to determine the permittivity of the analyte; and
  coupling the SAW and SPR sensors through a common substrate.

19. The method as defined in claim 18, wherein the step of coupling the SAW and SPR sensors includes the step of coupling the SAW to the SPR through an acousto-optic tunable filter (AOTF).

20. The method as defined in claim 18, wherein the step of coupling the SAW and SPR sensors includes configuring a chemically sensitive film to be shared by both the SPR sensor and the SAW sensor.

21. A method for evaluating an analyte comprising the steps of:
  utilizing a surface acoustic wave (SAW) sensor to determine the mass of the analyte;
  utilizing a surface plasmon resonance (SPR) sensor to determine the permittivity of the analyte; and
  generating an output signal that is based upon a combined state of both the SAW sensor and the SPR sensor, the output signal reflecting a quality of the analyte.

22. The method as defined in claim 21, wherein the step of generating an output more specifically includes generating a positive output only if both the SAW sensor and the SPR sensor generate a positive output.

23. The method as defined in claim 21, wherein the step of generating an output more specifically includes generating a positive output if either the SAW sensor or the SPR sensor generates a positive output.

24. A surface plasmon resonance (SPR) sensor comprising:
  a transducer configured to generate acoustic waves;
  an acoustic-optic tunable filter (AOTF), responsive to the acoustic waves generated by the transducer;
  means for introducing a broadband optical signal to the AOTF;
  a chemically sensitive film disposed in an output path of the AOTF; and
  a detector configured to monitor a transmissivity output of the chemically sensitive film.

25. The SPR sensor as defined in claim 24, further including an acoustic absorber interposed between the AOTF and the chemically sensitive film.

* * * * *

UNITED STATES PATENT AND TRADEMARK OFFICE
CERTIFICATE OF CORRECTION

PATENT NO.   : 6,161,437
DATED        : December 19, 2000
INVENTOR(S)  : Kevin F. Brennen, William Danies Hunt It is certified that error appears in the above-identified patent and that said Letters Patent is hereby corrected as shown below:

Column 2,
Line 13, delete the word "external".
Line 16, after the word "sample", delete the numeral "7".
Line 58, after the word "and", delete the word "has", and substitute therefor -- have --.

Column 3,
Line 51, after the word "at", add the word -- which --.
Line 52, after the word "frequency", delete the word "win", and substitute therefor -- will --.

Column 4,
Line 43, after the word "transducer", delete the numeral "22", and substitute therefor -- 20 --.
Line 47, after the word "transducer", delete the numeral "22", and substitute therefor -- 20 --.
Line 49, after the word "transducer", delete the numeral "22", and substitute therefor -- 20 --.
Line 52, after the word "transducer", delete the numeral "22", and substitute therefor -- 20 --.

Column 6,
Line 52, after the word "chemically", add the word -- sensitive --.

Column 9,
Line 34, after the phrase "FIG. 4", delete the word "is", and substitute therefor -- it --.
Line 53, after the word "includes", delete the word "a", and substitute therefor -- an --.

Claims,
Column 11, claim 11,
Line 3, delete the word "utiizing", and substitute therefor -- utilizing --.

UNITED STATES PATENT AND TRADEMARK OFFICE
CERTIFICATE OF CORRECTION

PATENT NO. : 6,161,437
DATED : December 19, 2000
INVENTOR(S) : Kevin F. Brennen, William Danies Hunt It is certified that error appears in the above-identified patent and that said Letters Patent is hereby corrected as shown below:

Column 12, claim 21,
Line 15-17, delete the phrase:

Signed and Sealed this

Twenty-seventh Day of November, 2001

*Attest:*

*Attesting Officer*

NICHOLAS P. GODICI
*Acting Director of the United States Patent and Trademark Office*